US010816441B2

(12) United States Patent
Zimbron

(10) Patent No.: US 10,816,441 B2
(45) Date of Patent: Oct. 27, 2020

(54) IN SITU MEASUREMENT OF SOIL FLUXES AND RELATED APPARATUS, SYSTEMS AND METHODS

(71) Applicant: E-Flux, LLC, Fort Collins, CO (US)

(72) Inventor: Julio Zimbron, Fort Collins, CO (US)

(73) Assignee: E-Flux, LLC, Fort Collins, CO (US)

( * ) Notice: Subject to any disclaimer, the term of this patent is extended or adjusted under 35 U.S.C. 154(b) by 80 days.

(21) Appl. No.: 15/150,157

(22) Filed: May 9, 2016

(65) Prior Publication Data

US 2016/0327456 A1   Nov. 10, 2016

Related U.S. Application Data

(60) Provisional application No. 62/158,823, filed on May 8, 2015, provisional application No. 62/159,445, filed on May 11, 2015.

(51) Int. Cl.
*G01N 1/22* (2006.01)
*G01N 33/24* (2006.01)

(52) U.S. Cl.
CPC ......... *G01N 1/2294* (2013.01); *G01N 1/2214* (2013.01); *G01N 33/24* (2013.01)

(58) Field of Classification Search
CPC .... G01N 1/2214; G01N 1/2294; G01N 33/24; G06F 11/30; G06F 21/55; G06F 21/554; G06F 21/606; G06F 21/6281
USPC ............ 73/432.1, 864.73, 864.74; 166/252.1
See application file for complete search history.

(56) References Cited

U.S. PATENT DOCUMENTS

| | | | | |
|---|---|---|---|---|
| 3,862,576 A | * | 1/1975 | Pogorski | G01V 5/02 73/19.09 |
| 4,468,558 A | * | 8/1984 | Malmqvist | G01V 5/02 250/253 |
| 4,801,800 A | * | 1/1989 | Scheible | G01T 1/178 250/255 |
| 4,847,494 A | * | 7/1989 | Alvarez | G01T 1/178 250/253 |
| 4,880,973 A | * | 11/1989 | Reynolds | G01N 1/2294 250/253 |
| 5,355,739 A | * | 10/1994 | Cooper | E21B 49/084 422/83 |

(Continued)

FOREIGN PATENT DOCUMENTS

CA    2547413 A1 * 11/2006 ............. G01N 33/24

*Primary Examiner* — Randy W Gibson
*Assistant Examiner* — Gedeon M Kidanu
(74) *Attorney, Agent, or Firm* — Davis, Brown, Koehn, Shors & Roberts, P.C.; Matthew Warner-Blankenship

(57) ABSTRACT

The disclosed apparatus, systems and methods relate to measuring the ability of the soil to transport gases at any location of the soil column, rather than just the flow of gases out of the soil. This enables the measurement of gas transport for various reactive and non-reactive species that often do not reach the ground level, such as methane, as it is used by microbes as a carbon source when there is sufficient oxygen for aerobic respiration. Thus, the invention helps understand transport and reactive processes at different locations in the soil, rather than just the limited information available at ground level. The disclosed apparatus, systems and methods relate to conducting microcosm studies in situ which enables direct estimates of degradation rate of specific soil contaminants.

19 Claims, 11 Drawing Sheets

(56) References Cited

U.S. PATENT DOCUMENTS

| | | | | |
|---|---|---|---|---|
| 5,744,730 A * | 4/1998 | Ballard | ................... | E21B 33/13 175/50 |
| 6,405,135 B1 * | 6/2002 | Adriany | ................... | F17D 5/02 702/22 |
| 6,649,129 B1 * | 11/2003 | Neal | ................... | G01N 1/16 422/88 |
| 7,972,082 B2 * | 7/2011 | Augenstein | ................... | B09B 1/004 405/129.95 |
| 2003/0136174 A1 * | 7/2003 | Edwards | ................... | G01N 1/2294 73/19.1 |
| 2004/0145379 A1 * | 7/2004 | Buss | ................... | G01N 33/246 324/664 |
| 2007/0243023 A1 * | 10/2007 | Augenstein | ................... | B09B 1/006 405/129.95 |
| 2007/0266800 A1 * | 11/2007 | Risk | ................... | G01N 1/22 73/863.23 |
| 2008/0008625 A1 * | 1/2008 | Thomas | ................... | G01N 21/3504 422/82.05 |
| 2009/0301234 A1 * | 12/2009 | Risk | ................... | G01N 1/2294 73/864.83 |
| 2011/0231099 A1 * | 9/2011 | Elkins | ................... | G01V 9/007 702/12 |
| 2012/0035850 A1 * | 2/2012 | Risk | ................... | G01N 1/2205 702/2 |
| 2012/0222500 A1 * | 9/2012 | Riess | ................... | G01N 1/02 73/863.23 |
| 2013/0031955 A1 * | 2/2013 | Zimbron | ................... | G01N 1/2294 73/23.42 |
| 2013/0235378 A1 * | 9/2013 | Nickerson | ................... | G01N 33/24 356/402 |
| 2013/0291622 A1 * | 11/2013 | Heinemeyer | ................... | G01N 1/2294 73/23.2 |
| 2015/0040658 A1 * | 2/2015 | Abyzov | ................... | G01T 1/1606 73/199 |
| 2017/0146679 A1 * | 5/2017 | Cheng | ................... | E21F 11/00 |

\* cited by examiner

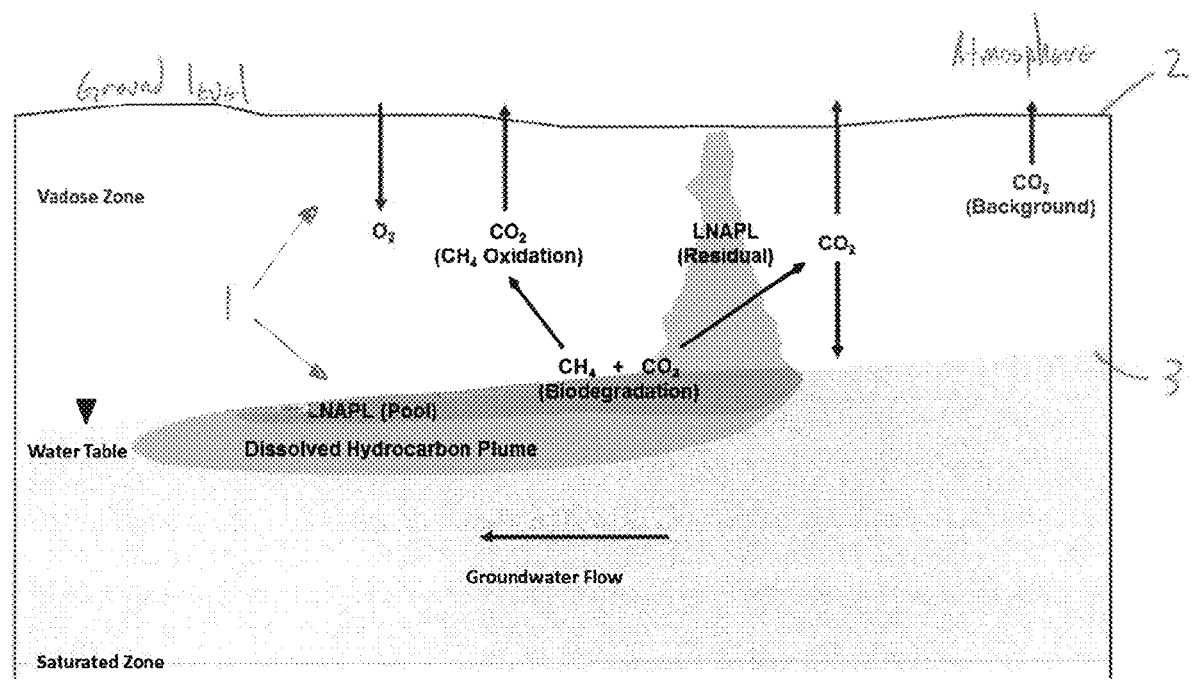
Figure 1 - (Prior Art)

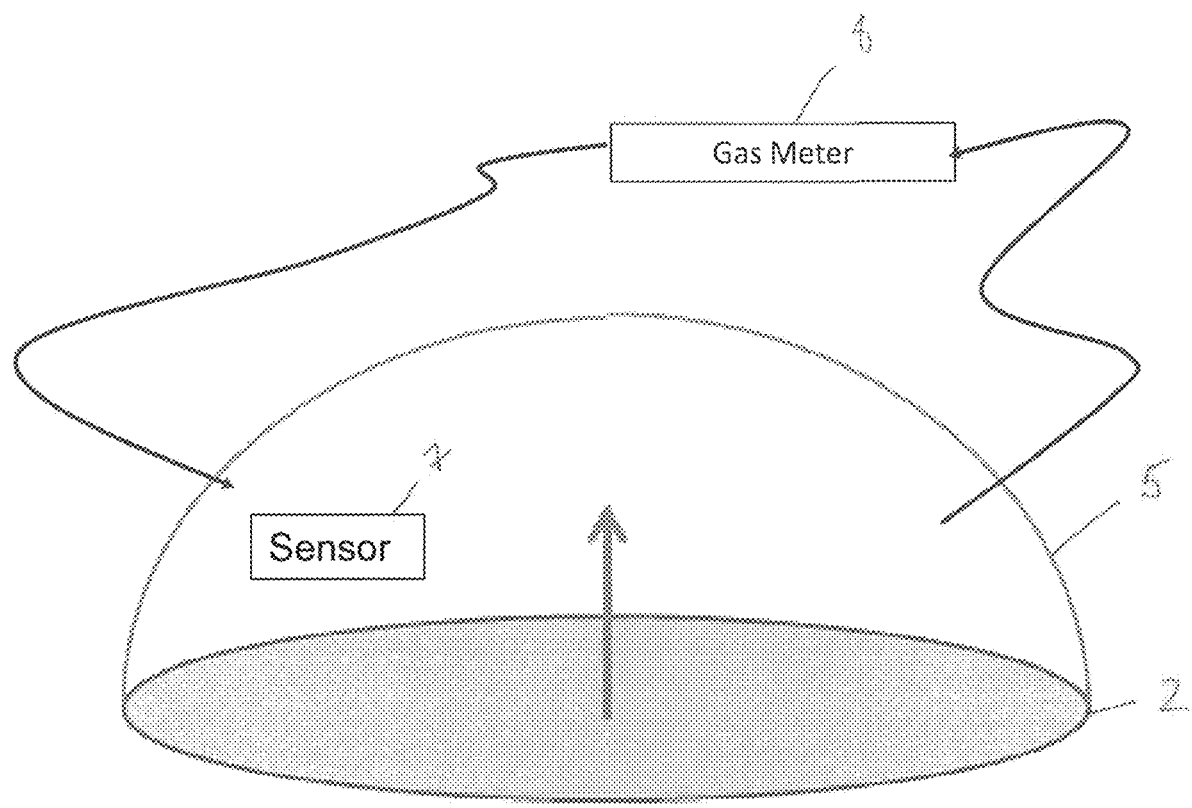
Figure 2 - Prior Art

FIG 4A (left). In situ flux chamber in inert gas flushing mode so as to create a concentration gradient.

FIG 4B (right). In situ flux chamber in flux measuring mode by recirculating gases within the chamber

IN SITU MEASUREMENT OF SOIL FLUXES AND RELATED APPARATUS, SYSTEMS AND METHODS

CROSS-REFERENCE TO RELATED APPLICATION(S)

This application claims the benefit of priority of U.S. Provisional Patent Application No. 62/158,823, filed May 8, 2015 and U.S. Provisional Patent Application No. 62/159,445, filed May 11, 2015, which are each incorporated herein by reference in their entirety.

TECHNICAL FIELD

The disclosure relates to apparatus, systems and methods for analyzing the flux of soil gases in situ. Certain implementations relate to the measurement of gas concentration and/or pressure in situ in establishing the flux.

BACKGROUND

It is known that subsurface organic contaminants and associated degradation products can occur as gas phase constituents in soil gas. In the case of releases of light non-aqueous phase liquids (LNAPL), the mass flux of carbon dioxide ($CO_2$), a common degradation product, provides an indicator of losses of LNAPL through natural attenuation processes. Natural attenuation of LNAPL bodies can occur at rates that rival or exceed conventional LNAPL recovery technologies. In fact, LNAPL losses to the gas phase by volatilization and biodegradation may be as much as two orders of magnitude larger than those due to dissolution into groundwater. Biodegradation, largely driven by methanogenesis, may overcome the dominant LNAPL mass loss process over time as the more biodegradable volatile components are quickly lost from the LNAPL. Numerical modeling and field measurements using multilevel gas samplers show that degradation-generated methane can be converted to carbon dioxide relatively quickly in the subsurface, and that greater than 98% of the carbon produced by biodegradation exits the ground surface as $CO_2$.

There is a need in the art for improved apparatus, systems and methods for measuring the degradation rates of contaminants in soil.

BRIEF SUMMARY

Discussed herein are various apparatus, systems and methods relating to the in situ measurement of soil gas fluxes, namely the transport of a specific chemical species within the soil.

In one Example, a system for in situ measurement of soil mass fluxes of a gas species present in soil gas, including: a chamber emplaced in a well in the soil and a gas concentration device configured to measure soil gas flux in situ.

Implementations may include one or more of the following features. The system further including a pressure sensor disposed within the chamber. The system further including a plurality of conduits in gaseous communication with the chamber. The system where the gas concentration device is further configured to establish initial concentration and pressure and configured to estimate advective fluxes. The system where the system is configured to flush the chamber with inert gas and then measure change in concentration of a gas species over time. The system further including a sorbent for a species of interest, where the sorbent is configured to sorb the species of interest. The system where the sorbent is disposed in a cartridge. The system where the sorbent is disposed in the chamber. The system where the chamber includes an inner opening and the sorbent is disposed within the inner opening. The method where the chamber is in operable communication with a gas concentration meter. The method where the chamber is in operable communication with a plurality of conduits leading out of the chamber. The method where the chamber is in operable communication with a pressure sensor. The method further including: establishing a pressure inside the chamber and a concentration of at least one gas of interest and flushing the chamber with inert gas by way of at least one conduit. The method where the chamber includes a selectively-permeable outer shell disposed around a selectively-permeable inner container. The device where the inner container and the outer shell are fluid permeable. The device further including a contaminant of interest, where the inner container includes an inner opening further including native soil seeded with the contaminant of interest. The device further including a second sorbent, where the contaminant is immobilized within the inner opening by way of the second sorbent such that the contaminants remain in the inner container. The device where the sorbent is spiked with contaminants to be degraded and/or with compounds to inhibit the degradation of contaminants to be used as abiotic controls. Implementations of the described techniques may include hardware, a method or process, or computer software on a computer-accessible medium.

In one Example, a method for in situ measurement of soil mass fluxes, including: emplacing a chamber in a soil sample of interest and establishing a flux of at least one gas of interest by way of the change in concentration of a species over time in the chamber. Other embodiments of this aspect include corresponding computer systems, apparatus, and computer programs recorded on one or more computer storage devices, each configured to perform the actions of the methods.

Implementations may include one or more of the following features. The method where the chamber is in operable communication with a gas concentration meter. The method where the chamber is in operable communication with a plurality of conduits leading out of the chamber. The method where the chamber is in operable communication with a pressure sensor. The method further including: establishing a pressure inside the chamber and a concentration of at least one gas of interest and flushing the chamber with inert gas by way of at least one conduit. The method where the chamber includes a selectively-permeable outer shell disposed around a selectively-permeable inner container. The device where the inner container and the outer shell are fluid permeable. The device further including a contaminant of interest, where the inner container includes an inner opening further including native soil seeded with the contaminant of interest. The device further including a second sorbent, where the contaminant is immobilized within the inner opening by way of the second sorbent such that the contaminants remain in the inner container. The device where the sorbent is spiked. Implementations of the described techniques may include hardware, a method or process, or computer software on a computer-accessible medium.

In one Example, a device for in situ microcosm studies in soil, including a double walled container further including an inner container and an outer shell configured to be disposed in the soil, an inner opening, an outer opening, and at least one sorbent, where the inner container and outer shell are selectively permeable, so as to allow flow of at least one off groundwater and gases through the container. Other embodiments of this aspect include corresponding computer systems, apparatus, and computer programs recorded on one or more computer storage devices, each configured to perform the actions of the methods.

Implementations may include one or more of the following features. The device where the inner container and the outer shell are fluid permeable. The device further including a contaminant of interest, where the inner container includes an inner opening further including native soil seeded with the contaminant of interest. The device further including a second sorbent, where the contaminant is immobilized within the inner opening by way of the second sorbent such that the contaminants remain in the inner container. The device where the sorbent is spiked.

In these examples, system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. Implementations of the described techniques may include hardware, a method or process, or computer software on a computer-accessible medium.

While multiple embodiments are disclosed, still other embodiments of the disclosure will become apparent to those skilled in the art from the following detailed description, which shows and describes illustrative embodiments of the disclosed apparatus, systems and methods. As will be realized, the disclosed apparatus, systems and methods are capable of modifications in various obvious aspects, all without departing from the spirit and scope of the disclosure. Accordingly, the drawings and detailed description are to be regarded as illustrative in nature and not restrictive.

BRIEF DESCRIPTION OF THE DRAWINGS

FIG. 1 depicts processes resulting in the production of soil gas $CO_2$ and soil gas flux in the vadose zone.

FIG. 2 is a schematic overview of various prior approaches to measuring soil gas flux.

DETAILED DESCRIPTION

Figure 3A:
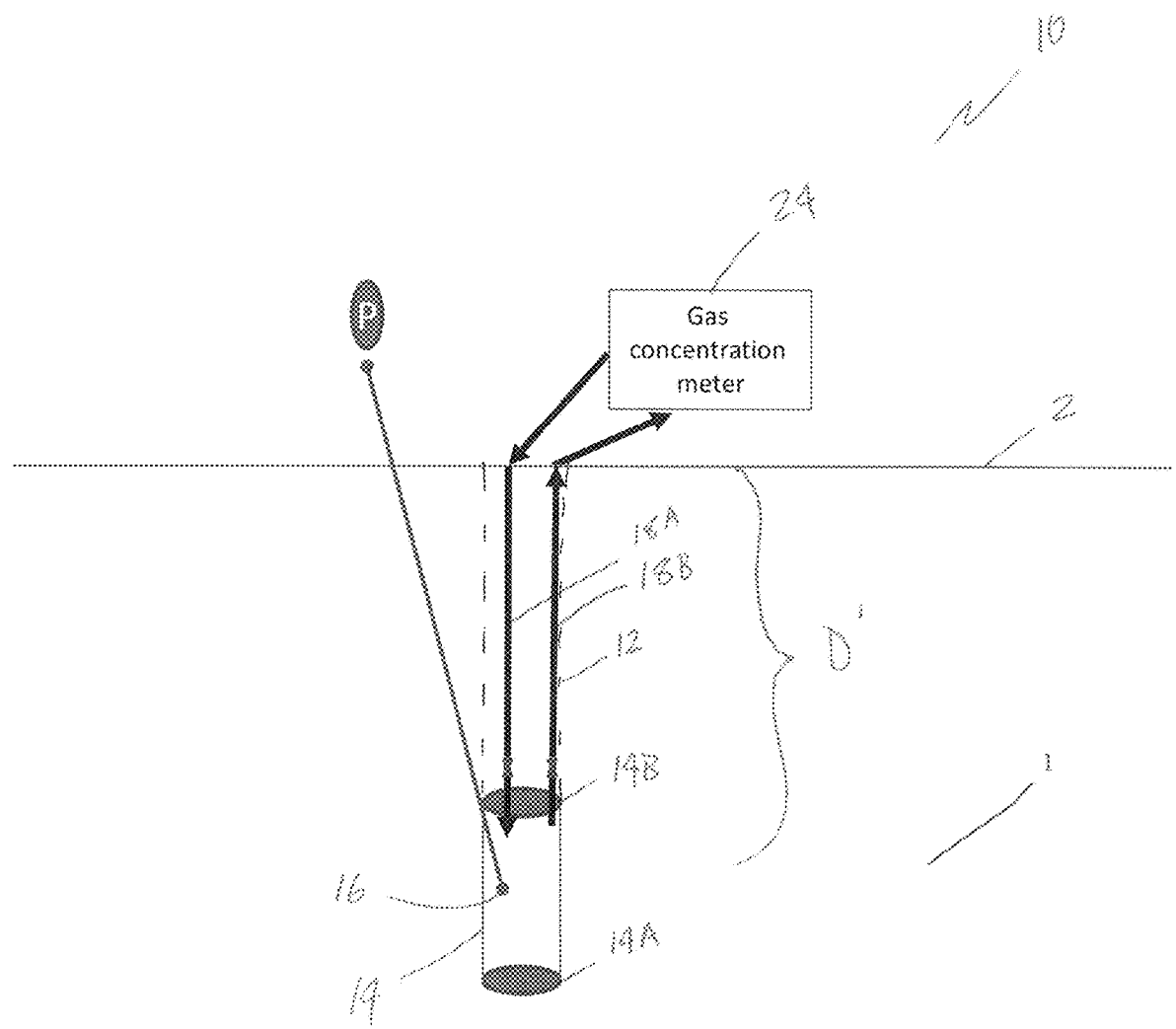
FIG. 3A is a schematic side view of a flux measuring system with a permanent chamber, according to an exemplary implementation.

The presently disclosed apparatus, system and method relate to in situ flux measurement within discrete locations of the vadose zone. It is understood that the presently-disclosed in situ system 10 represents a significant improvement over the prior art because it enables the measurement of the soil to transport gases throughout the soil column, rather than just the flow of gases out of the soil at ground level. It is understood that the various implementations described herein can be incorporated and used with other flux monitoring methods, such as those described in co-pending U.S. application Ser. No. 15/137,958, filed Apr. 25, 2016 and entitled "Establishment of Contaminant Degradation Rates is Soils Using Temperature Gradients, Associated Methods, Systems and Devices," the various devices, systems and methods of which are incorporated herein by reference in their entirety.

As shown in the drawings, in exemplary embodiments of the in situ system 10, a chamber 14 is created within the vadose zone 1, rather than at ground surface. As described herein, in certain applications a chamber 14 is disposed within the soil column or a well 12 and a pressure probe 16 is inserted into the chamber 14. A gas concentration meter 20 is also provided. Accordingly, the various implementations of the system 10 are configured to measure soil gas flux in situ. In certain exemplary embodiments, at least one novel permeable or semi-permeable in situ device 50, 100 is provided that can be mounted on a non-permanent soil probe, driven by a direct push drilling equipment. The in situ device 50, 100 is emplaced into a soil location, measurements are conducted. In these implementations, the in situ device 50, 100 can be configured to assess the concentration of a species of interest within the soil or well 12.

Accordingly, the disclosed implementations of the system 10 enable the measurement of gas transport for reactive species or contaminant vapors that often do not reach the ground level. One such contaminant vapor is benzene, or contaminant intermediates such as methane gas, which is used by microbes as a carbon source at locations close to ambient air where there is sufficient oxygen for aerobic respiration. Thus, the system 10 allows the user to understand transport and reactive processes at different locations in the soil, rather than just the limited information available at ground level.

Turning to the figures in greater detail, the various implementation of the system 10 relate to the measurement of in situ reactions at a range of depths within the vadose zone 1. As is shown in FIG. 1, the vadose zone 1 is a porous region located between ground level 2 and the groundwater table 3. The majority of the pores in the vadose zone are filled with soil gases. Prior art above-ground methods for measuring the flux out of the soil have been established. These above-ground methods generally evaluate the mass discharge per unit time per area of ground surface. Two such direct methods are the closed chamber method and open-flow passive soil traps.

As best shown in FIG. 2, the prior art chamber method consists of locating a chamber 5 at ground surface 6 and estimating the gaseous efflux, or "flux," into the chamber by tracking changes in concentration within the chamber. In certain prior art implementations, a sensor 7 may be placed within the chamber 5. In alternate prior art implementations, a gas meter 8 can be mounted outside the chamber, such that sampling may occur outside the chamber and the air recirculated back by way of a pump. In either implementation, a mass balance through the area of contact with soil enables a calculation of the flux:

$$\text{Flux} = \frac{\frac{\Delta C}{\Delta t} \times \text{Volume}_{chamber}}{\text{Area}} \qquad (\text{Eq. 1})$$

where C is the soil gas concentration within the chamber, $\text{Volume}_{chamber}$ is the volume of the chamber, and Area is the area of contact between the soil and the chamber.

One limitation the previous above-ground approaches is that they require the ground surface 6 to be permeable to gases. It is understood that in sites covered with concrete or asphalt, or where the soil lithology includes clay layers saturated with water—such as following a large rain, there may be little to no gas permeability of the surface. Furthermore, the processes resulting from soil gas fluxes at grade are numerous and often sequential. By way of example, generation of $CO_2$ soil gas fluxes at grade results from partitioning of contaminants into soil gases, methanogenesis of petroleum, and methane oxidation, coupled with the associated transport processes through the soil.

Further, the flux of gases changes the concentrations of those gases within the chamber 5 and can cause corresponding changes in the concentration gradient. These gradient changes reduce the measured flux, introducing a bias known as the "chamber effect." It is understood that in prior art applications of the chamber method at the ground level 2 (such as those shown in FIGS. 1-2), the chamber effect can be minimized by limiting data collection to times shortly after emplacing the chamber.

Turning to the various embodiments of the present in situ chamber system 10, FIG. 3A depicts an implementation of the system 10 in flux metering mode (described further in relation to FIG. 4B below). In the implementation of FIG. 3A, a chamber 14 is installed in a well 12 at a known depth D' below ground using a "permanent" pressure sensor probe 16. It is understood that the well 12 can be a pre-existing or new opening in the soil. In certain implementations, the well 12 can be pre-fitted with a permeable, selectively-permeable or semi-permeable casing material—such as slotted PVC—to prevent collapse or deformations.

The prior art, at grade chamber method begins with ambient concentrations of the species of interest at low levels, such as situations where the concentrations in the ambient air are typically approaching zero. In contrast, the presently disclosed system 10 is configured to estimate the changes in chamber 14 gas concentrations over time upon a minimal perturbation from the native soil gas concentrations. These implementations thereby avoid creating large concentration gradients resulting in larger fluxes into the chamber than those prevailing in the soils. Various embodiments are also applicable to high soil gas concentrations as well, in contrast to the above-described chamber method.

Figure 3B:
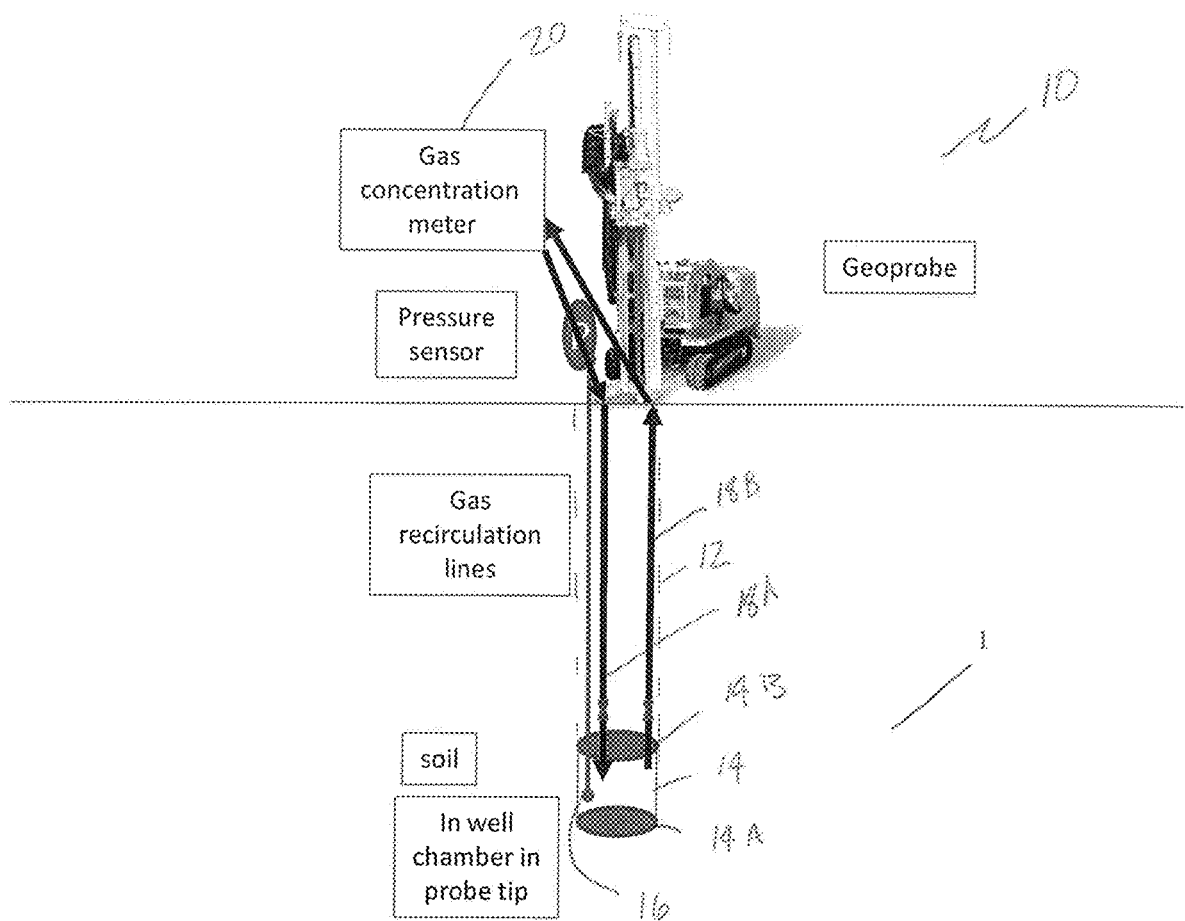
FIG. 3B is a schematic side view of a flux measuring system with a temporary chamber, according to a further exemplary implementation.

Continuing with the implementation of FIGS. 3A-B, the in situ chamber 14 is formed by isolating a permeable region—such as a screened or slotted section—of a well 12 by sealing a bottom chamber end 14A and an upper chamber end 14B with packers—inflatable well plugs typically made of rubber and steel that are gas impermeable. In these embodiments, a plurality of small conduits 18A, 18B, or gas recirculation lines, are connected to the chamber 14—such as through air-tight openings in the upper chamber end 14B (not shown) so as to be in gaseous communication and permit or encourage the flow of gasses into 18A and out of 18B the chamber as well as gas mixing within the chamber 14. It is understood that in the exemplary implementations, several chambers 14 can be disposed within a single well 12, and that several wells can be used within an individual vadose zone 1 or site.

It is therefore understood that in certain exemplary embodiments the system 10 can utilize a non-permanent probe 16 transiently placed in a well 12 or other opening in the soil, in certain embodiments by a machine. In some embodiments, the probe 16 can be re-located to a subsequent location after completing data collection in a location, such as by direct push drilling equipment or the Geoprobe depicted in FIG. 3B. In these embodiments, the system 10 is capable of taking a variety of flux measurements to assess the rate of degradation or other characteristics of certain reactive compounds, production of reaction products, or flow of species that are not reactive.

In the implementation of FIG. 3B, the system 10 uses a non-permanent chamber 14. In these implementations, the non-permanent chamber 14 is again formed with by a bottom chamber end 14A and a top chamber end 14B emplaced in the soil column "well" 12. It is understood that in these implementations, a permanent open well 12 may not actually exist, instead, the well 12 can simply represent a section of the soil column in which the chamber 14 is created.

In these implementations a non-permanent probe 16 is extended into the chamber 14. Again, a plurality of small conduits 18A, 18B, or gas recirculation lines, are connected to the chamber 14 as described above. In these implementations, the depth of the probe 16 can be adjusted to collect data from several depths, such as by direct push drilling equipment 24, such as a geoprobe. It is understood that in alternate embodiments, other established methods may be used to dispose the probe 22 at one or more depths.

Continuing with FIGS. 3A-3B, in exemplary embodiments, in addition to the pressure sensor 16, the system 10 has a gas concentration meter 20 to measure the pressure inside the chamber 14 and the gas flow out of the chamber 14 or associated with recirculation flow. After emplacing the chamber 14 and establishing the baseline concentration and pressure, the conduits 18A, 18B in connection to a gas pump serve to introduce a pure inert gas—such as helium—into the chamber 14 to dilute or "flush" the gases from the chamber, thereby decreasing the concentration of the species of interest, for example $CO_2$. In certain embodiments, the outflow of gases from the chamber 14 is substantially matched to the inflow, so there would be no net advective flow in or out of the chamber 14, and the pressure within the chamber stabilizes to the same as it was without flow.

In exemplary implementations, pressure stabilization can be achieved with the gas recirculation lines or conduits, as is shown in FIGS. 3A-B. In these implementations, the gas concentration meter 20 is in gaseous communication with the outflow line, vent and inflow line, so as to be capable of directing the gas flow in either direction. Following this inert gas flush, the flux can be established in the chamber 14 as described herein.

FIGS. 4A-4B depict various implementations of the system 10 in use. Although the principles of operation and data analysis of the system 10 are the same for the various implementations, for brevity the operation of the implementations will be explained herein with reference to the use of an existing well 12. It is further understood that FIGS. 4A-4B depict implementations having both an in-chamber pressure sensor 16 and an external gas concentration meter 20, though the system 10 can function with only one of the sensor 16 or the meter 20.

Figure 4:
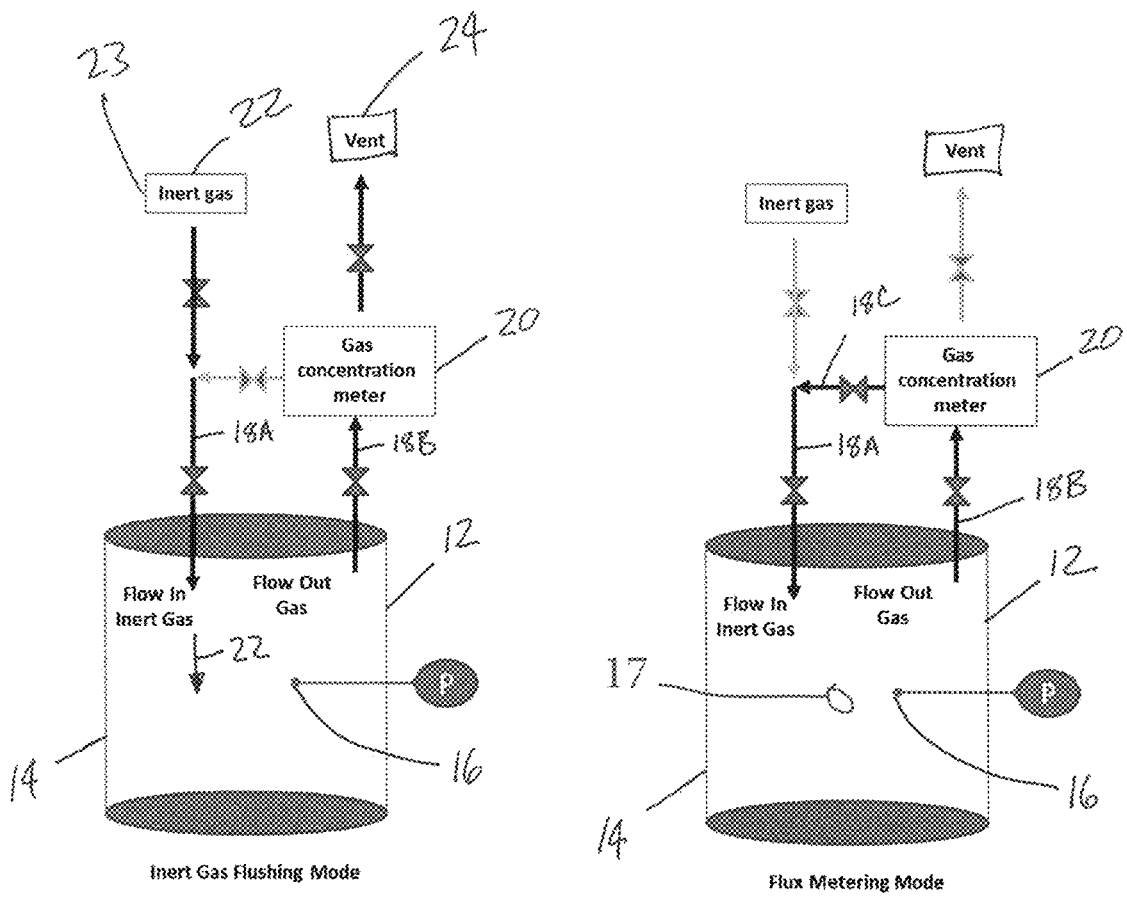
FIG. 4A is a schematic side view of a flux measuring system chamber in gas flushing mode, according to an exemplary implementation.
FIG. 4B is a schematic side view of a flux measuring system chamber in flux measuring mode, according to an exemplary implementation.
FIG. 4C is a schematic representation of the system, according to an exemplary implementation.
Figure 5A:
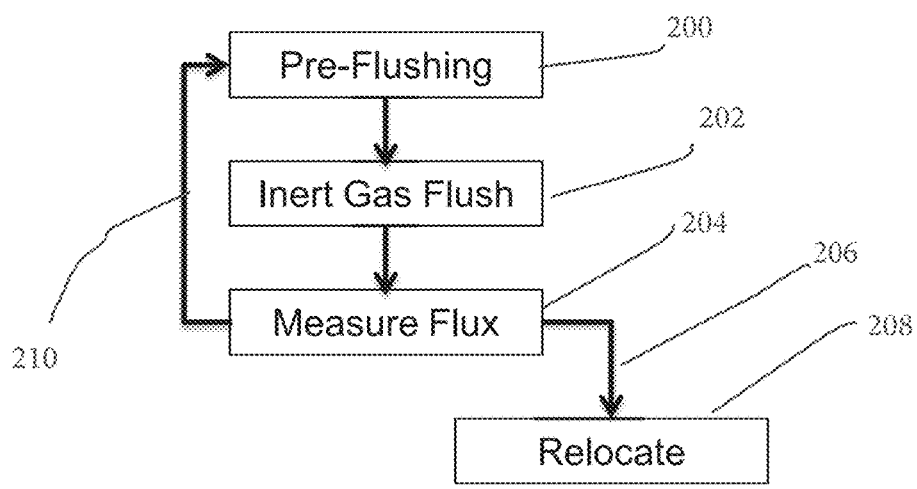
FIG. 5A is a flow chart depicting the possible operation of a chamber of the system, according to exemplary implementations.
Figure 5B:
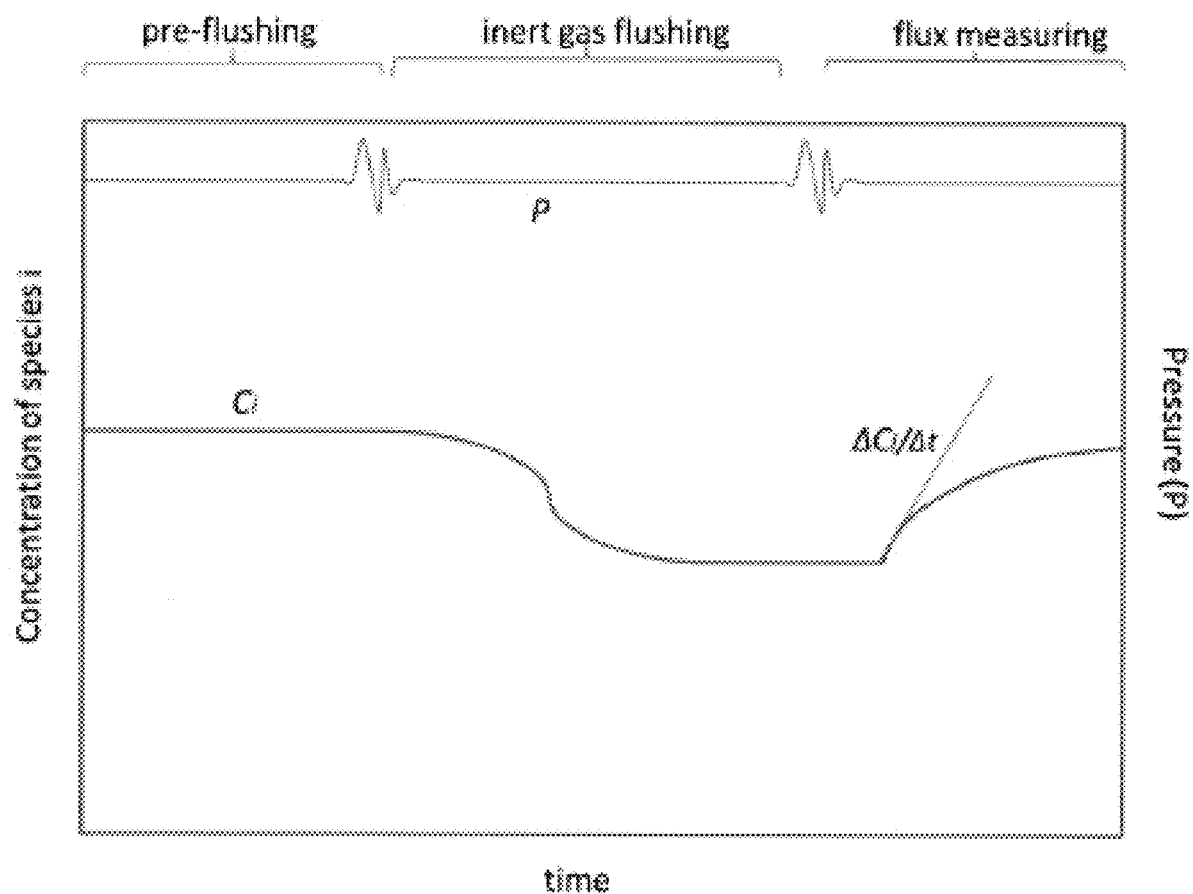
FIG. 5B is a graph depicting exemplary pressure and concentration of the chamber and a species of interest over time, according to the various steps of FIG. 5A.

In FIG. 4A, an in situ flux chamber 14 is disposed within a well 12 and is being operated in inert gas flushing mode so as to create a concentration gradient. As shown in FIGS. 5A-B, in these implementations the concentration over time can therefore be established after the chamber (shown in FIGS. 3A-4B at 14) has been emplaced, and is shown as "pre-flushing." As shown in the implementation of FIG. 4A, after the "pre-flushing" concentration has been established, inert gas 22 from an external source 23 can be applied to the chamber 14 through the inflow conduit 18A to create a concentration gradient within the chamber 14, and the gas from within the chamber is allowed to exit through a vent 24 in communication with the outflow conduit 18B. This "inert gas flushing" is also shown in FIGS. 5A-B, as are other possible stages or steps in the use of the system 10 according to these implementations.

As shown in the implementation of FIG. 4B, the in situ flux chamber 14 is shown in flux measuring mode (also shown in FIGS. 5A-B) by recirculating gases within the chamber, wherein there is no net flow in or out, but the gasses are being continually redirected through the chamber and concentration meter. As shown FIG. 4B, after the concentration gradient is established in the chamber 14, the inflow conduit 18A and outflow conduit 18B are brought into direct communication, for example by a recirculation conduit 18C, so as to recirculate gas within the chamber 14 and through the gas concentration meter 20.

Continuing with the implementation of FIG. 4B, the concentration of the species of interest inside the chamber 14 can therefore be monitored with a concentration sensor 17 within the chamber 14 and/or a real real-time gas meter 20. Changes in concentration can be recorded in a database, data logger, or other data storage system known in the art (not shown). It is understood that in certain embodiments, the "dead space" of the tubing can be minimized to avoid delays in the concentration response time at the by the gas concentration meter alone. However, dead space minimization is not required if monitoring the gas concentrations occurs within the chamber 14 by way of an in-chamber concentration sensor 17.

Figure 4C:
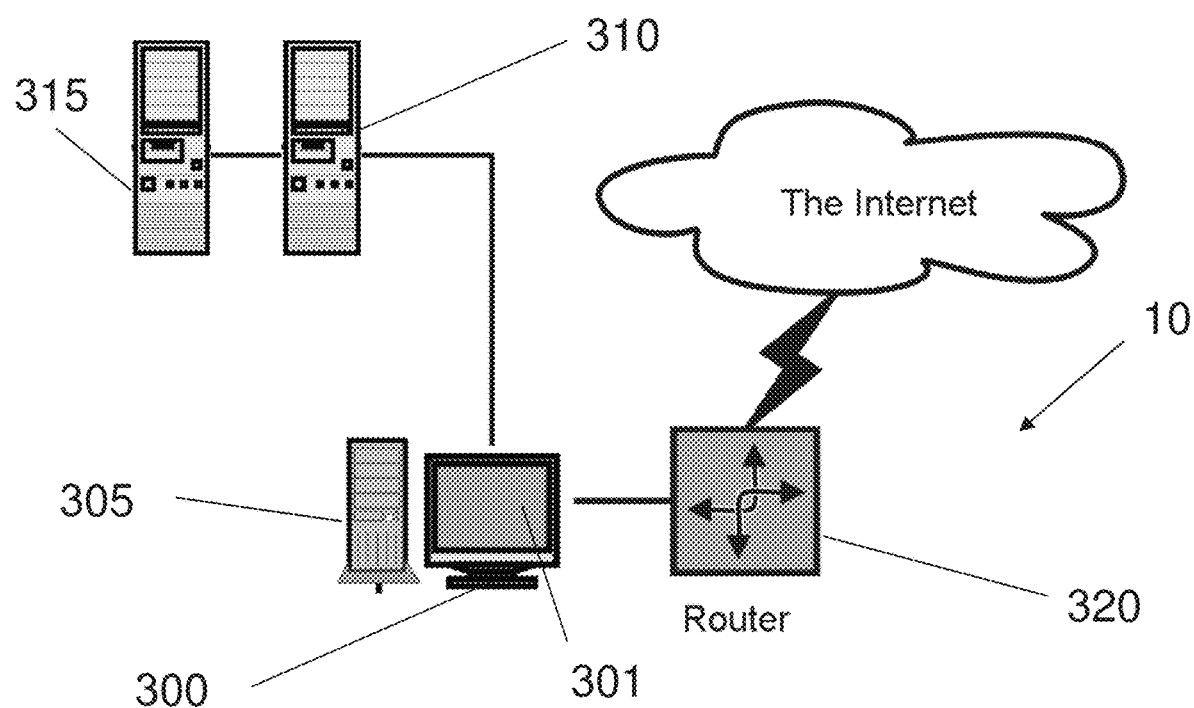

According to one embodiment, as shown in FIG. 4C, the system 10 also has the server or processor or processors 300 running reaction rate estimation software 301. The processor 300 comprises a central processor unit ("CPU") and main memory, an input/output interface for communicating with various databases, files, programs, and networks (such as the Internet), and one or more storage devices. The storage devices may be disk drive devices or CD-ROM devices. The processor 300 may also have a monitor or other screen device and an input device, such as a keyboard, a mouse, or a touch sensitive screen and may be connected to a network 105.

According to one implementation, the processor 3 is in communication with at least one soil database 310. According to one embodiment, the soil database 310 contains information regarding the concentration, pressure, time, temperature and/or depth at each temperature measurement device around the reactive zone, and the accumulation of any other kind of information relating to each temperature measurement device, or chamber 14A, 14B, 14C, 14D. A parameter database 315 may also be in communication with the processor 300. The parameter database 315 contains information relating to any particular reactive zone, such as contaminant information, reactive zone size information, soil characteristics and the like.

It is understood that the processor 300 can be any computer known to those skilled in the art. In one embodiment, the central processor 300 includes a website hosted in at least one or more computer servers. It is understood that any system disclosed herein may have one or more such server 105 and that each server may comprise a web server, a database server and/or application server, any of which may run on a variety of platforms.

In one implementation, the central processor 300 includes software programs or instructions to process requests and responses. These software programs or instructions perform calculation, compilation, and storage functions, transmit instructions, and generate reports. It is understood that any embodiment of the systems 10 disclosed herein that provide for data collection, storage, tracking, and managing can be controlled using software associated with the system. It is further understood that the software utilized in the various embodiments described herein may be a software application or applications that are commercially sold and normally used by those skilled in the art or it may be a specific application or applications coded in a standard programming language.

It is further understood that the software can be any known software for use with the systems described herein to track, calculate, and manage the various parameters as described herein. For example, as described in further detail herein, various embodiments of the systems described herein could have any one or more of software for tracking time, temperature, corrections, soil characteristics, contaminant information, or software allowing for optimization of any one of these parameters.

The processor 300 allows access to various network resources. In one embodiment, the central processor 300 also has access, via the network 320 or some other communication link, to external data sources that may be used to keep the information in the databases current. In one implementation, a number of site computers may be connected to the server at any given time, and therefore a number of facilities or locations may utilize the system simultaneously.

In the system 10, generally, reactive zone data (such as, for example, pressure and concentration data, etc.) entered into the system 10 via a client computer or processor 300 is received by the processor 300 or server 305 and stored in any of the appropriate databases of the system.

The databases 310, 315 serve as the inputs to and information storage for the system 10, which processes the information as described below and generates any one or more of notifications, reports, work orders, suggested actions, and/or instructions to a user or to a piece of equipment or a third party system.

Continuing with FIGS. 3A-4C, in various embodiments, gas concentrations can be measured using a variety of gas concentration meters 20, such as the RK Eagle II, Lantech 2000 Landfill Gas Meter, the RKI-85, for $CO_2$ only (low range, from 0-1%, or 1-10,000 ppmv), all of which come with an integrated air pump (at a fixed flow rate). This pump would have to be turned off and bypassed. An external, adjustable flow rate pump can be used to achieve the suitable flow rate, such as the GilAir5 or Tuff Personal Pump. In alternative embodiments, the concentration of compounds in gas can be measured using an on-line gas chromatograph ("GC") and the appropriate detector (for example mass spectra for petroleum hydrocarbons, or electron capture detector for chlorinated solvents). Field portable units are available, for example: HAPSITE GC-MS and Torion Tridion-9. It would be understood that other components can take the place of the meter 20 alternate embodiments, as is described further in relation to FIGS. 6-7.

Measurement of the pressure within the chamber 14 allows for various additional improvements over the prior art. First, the various implementations of the system 10 avoid large pressure gradients upon the flow of inert gases and therefore a net draw of advective flux in or out of the chamber. Second: in situ measurement permits measuring the native soil gas pressure ($P=P_{soil}$), in order to estimate advective soil gas fluxes (measured by differences in pressures at different locations within soils).

As is shown in FIGS. 5A-B, in exemplary embodiments of the in situ measurement system 10, pressure and concentration data collection can optionally comprise distinct optional stages. One such stage is pre-flushing (box 200), wherein a steady-state concentration of the species of interest—such as a gas—is established. Another stage is inert gas flushing (box 202), wherein a volume of inert gas is introduced into the chamber to "flush out" other gasses, such as the species of interest. Another stage is flux measurement (box 204), which is described in further detail herein. In certain implementations, following measurement, the chamber 14 or probe 16 can be re-located (line 206, box 208—as described in relation to FIG. 3B), or in alternate implementations the process can be repeated (box 210). It is understood that various additional stages may be contemplated, and that each of these stages is optional in certain implementations.

In certain implementations, the total flux $J_{T,i,z}$ of the species of interest i at a location z in the soil column can be measured by the system 10. In these implementations, the total flux consists of the summation of the advective and diffusive fluxes, such as is given by:

$$J_{T,i,z} = J_{adv,i,z} + J_{diff,i,z} \quad (Eq.\ 2)$$

$$J_{adv,i,z} = C_{i,z} \frac{k_G}{\mu_G} \frac{\Delta P}{\Delta z} \quad (Eq.\ 3)$$

$$J_{diff,i,z} = \frac{\frac{\Delta C_{i,z}}{\Delta t} \times \text{Volume}}{\text{Area}} \quad (Eq.\ 4)$$

where $C_{i,z}$ is the concentration of the species of interest i at the location z of the measurement,
Volume is the volume of the chamber,
Area is the surface area of the chamber available for exchange of gases with the surrounding soil excluding any packers (discussed below),
$k_G$ is the soil gas permeability, typically in units of length squared,
$\mu_G$ is the dynamic soil gas viscosity, typically in units of mass/(time×length), $\Delta P/\Delta z$ is the pressure gradient in the soil assuming a Darcy type of advective flow, and $\Delta C_{i,z}/\Delta t$ is the change of concentration within the chamber after flushing with the inert gas stops.

In these implementations, a measurement of the diffusive flux under Eq. 4 does not require estimation of in situ diffusion coefficient as was the case in the gradient method. The gradient method consists of the use of Fick's second law of diffusion, in which local concentration profiles with elevation and the in situ diffusion coefficient are fitted to a steady-state, diffusion only gas transport model.

As shown at box 200 in FIG. 5A, certain embodiments of the system 10 address the measurement of pressure and initial gas concentrations before inert gas flushing. Such measurements allow the user to establish the initial concentration and pressure to estimate advective fluxes (Eq. 3). In these embodiments, the pressure gradient associated with advective flux would be determined with respect the pressure at another location, for example a neighboring location (to determine a local advective flux estimate) or with respect to ground (to determine an overall, maximum potential flux).

Switching to inert gas flushing mode (box 202) results in minimal and short-term disturbances to pressures within the chamber 14, followed by a stabilization of soil gas concentrations and pressures within the chamber 14 during inert gas flushing. The pressure gradient ($\Delta P/\Delta z$) during inert gas flushing is required to be the substantially similar as the initial to avoid generation of net advective flux into or out of the chamber 14 (Eq. 3).

In certain embodiments, preventing the flow of inert gases which result in a rebound of gas concentrations within the chamber is important for proper analysis. In these implementations, the change in concentration over time forms the basis to estimate the diffusive flux $\Delta C_{i,z}/\Delta t$.

As an alternative to the determination of total flux based on the flux measurement (box 204), the diffusive flux into the chamber 14 in alternate implementations can be determined at steady state—which is achieved upon flushing the chamber with the inert gas—by using the steady state mass balance for a continuously stirred tank reactor ("CSTR"):

$$r_i = \frac{FR \times (C_{i,out} - C_{i,in})}{\text{Volume}} \quad (Eq.\ 5)$$

where FR is the flow rate of purging gas,
$C_{in}$ and $C_{out}$ are the concentrations of species i in inflow and outflow streams, and Volume is the volume of the chamber.

Because the purging or flushing gas inflow (box 202) does not contain the compound of interest, $C_{in}=0$, the mass per unit time generated within the chamber is equal to:

$$r_i \times \text{Volume} = FR \times C_{i,out} \quad (Eq.\ 6)$$

In circumstances where the net advective flux into the chamber is null, meaning that the pressure is equal to that before flushing the inert gas into the chamber, the diffusive flux into the chamber can be represented by the mass per unit time generation rate divided by the surface area available for gas exchange between the chamber and the surrounding soil—thus given by:

$$J_{diff,i,z} = \frac{r_i \times \text{Volume}}{\text{Area}} = \frac{FR \times C_{i,out}}{\text{Area}} \quad (Eq.\ 7)$$

In various implementations, the pressure drop through the conduits 18A, 18B can be described as:

$$\Delta p = 7.57 \frac{q^{1.85} L 10^4}{d^5 p} \quad \text{(Eq. 8)}$$

where $\Delta p$ is the pressure drop (kgf/cm2), L is the length of the pipe (m), d is the pipe diameter (mm), and p is the absolute pressure (kgf/cm2) at the pipe beginning.

Figure 6:
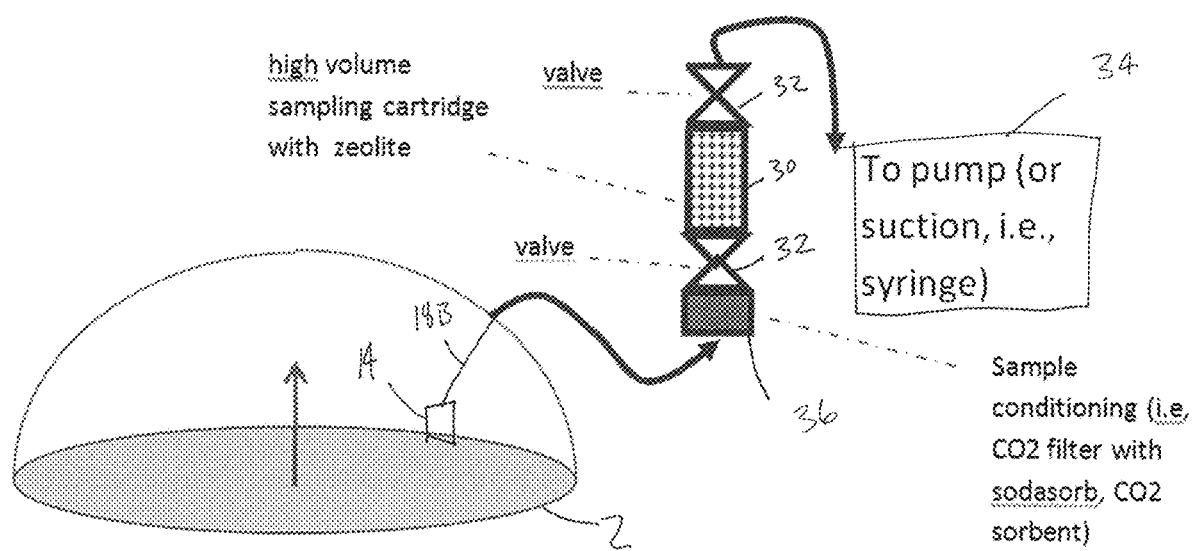
FIG. 6 depicts a schematic overview of an implementation of the system with a sampling cartridge and a real-time gas meter, according to one exemplary implementation.

As is shown in the implementation of FIG. 6, by applying Eq. 8 to an illustrative example having a chamber 14 about 10 m below the ground surface 2 and accounting for the conduits 18A, 18B, a 20 m long tube with a diameter of ¼" operating at a flow rate of 200 mL/min or less results in a negligible pressure drop: 1.24E-05 kgf/cm2, or 0.0012% with respect to atmospheric source pressure. Further, in this circumstance, the flow rate can be increased to 400 mL/minute and still result in a negligible pressure drop.

Analysis can include the total mass of the analyte, and the nature of the analyte (i.e., isotopic analysis that can be used to determine the source of the gas sampled by comparison with reported or measured data on the nature of the source). By conducting this analysis, the invention enables the calculation of soil gas flux by source type with much larger sensitivity than using field measurements or grab sample methods.

Figure 7:
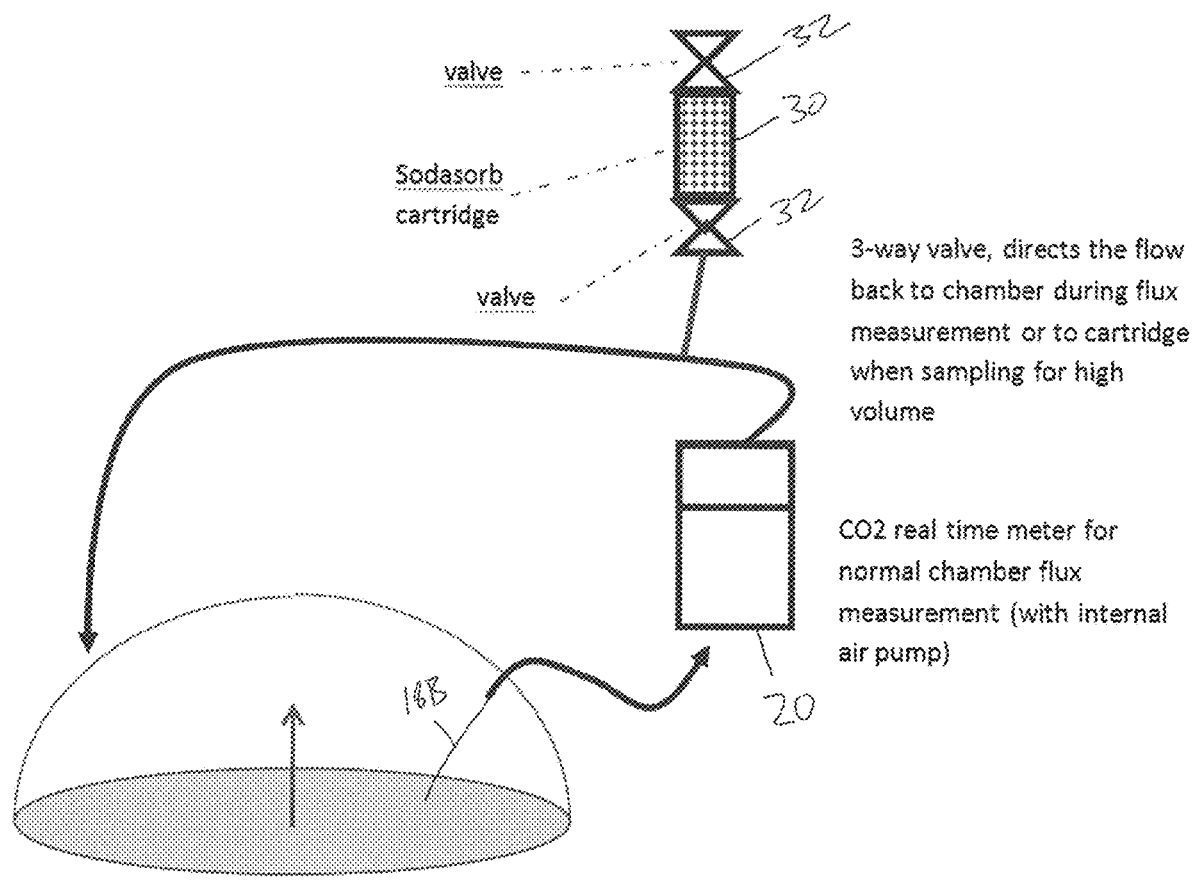
FIG. 7 depicts another schematic overview of an implementation of the system with a sampling cartridge, according to another exemplary implementation.

Certain further alternative embodiments, as described in relation to FIGS. 6-7 comprise a high volume sampling method in lieu of an on-site meter 20. In these implementations, a large volume of gas can be transferred from the chamber 14 into a small container that may contain a sorbent. In these implementations, the container and/or sorbent stabilizes the gas sample and then can be transported to an offsite lab, where the more sensitive and/or more cost effective laboratory methods can be used for analysis. The mass from a sample pre-concentrated in the field using these implementations is typically large: at least an order of magnitude larger than what is known in the art as "grab" samples. which decreases the detection limit and increases the sensitivity by the same factor. Further improvements in the analysis result from the use of laboratory instruments, rather than field portable ones.

As shown in FIG. 6, in certain exemplary embodiments of the system 10, $N_2O$ soil gas flux and contribution from nitrogen fertilizer can be estimated. In these embodiments, a chamber 14 is emplaced in the soil 2. A subsample of the chamber gas with a known volume (for example 1L) can be pumped through a sorbent cartridge 30, such as a Zeolite 5A cartridge, at a given time after chamber closure. In these embodiments, the cartridge 30 further comprises at least one valve 32.

As also shown in FIG. 6, certain implementations of the system 10 comprise a prefilter 36 in operable and gaseous communication with the chamber 14. As $CO_2$ interferes with the $N_2O$ absorption on zeolites, a prefilter 36 can be used in various implementations to sorb $CO_2$ can be placed on line prior to the filter in certain embodiments, as would be understood by the skilled artisan.

In various implementations, and as shown in FIGS. 6-7, valves 32 can be fitted to the cartridge 30. These valves 32 can be configured to open for sampling and close thereafter, such as during transportation to the lab. Nitrogen isotopes can be quantified in the sample, and compared to either the fertilizer used, or other sources of nitrogen available in the soil using a two source model.

As shown in FIG. 7, in certain embodiments, the valve 32 is a three-way valve, which is used to direct flow back into the chamber 14 during flux measurement or to the cartridge 30 when sampling high volumes. In further embodiments, the system further comprises a real-time CO2 meter (as depicted above at 20) for chamber flux measurement. In certain of these embodiments, an internal air pump 34 is also provided in the meter.

In exemplary embodiments, the cartridge 30 is retrieved and sealed for further transport for analysis in the lab at a later date. The ratio of sorbed mass of the gas of interest ($N_2O$) in the cartridge to the sample volume passed through the cartridge is equal to the concentration at the time of sampling. In certain embodiments, the sorbent for $N_2O$ comprises zeolites, a mineral material capable of sorbing $N_2O$ quantitatively and showing quantitative desorption for analysis.

In various implementations, samples of gas collected from the chamber 14 can be used to determine the concentration of $N_2O$ at different times of sampling in order to determine dC/dt in Eq. 1. $N_2O$ concentration in Zeolite is determined according to methods well known in the art. In certain implementations, samples are analyzed using a gas chromatograph equipped with an electron capture detector or other $N_2O$ detector. According to further exemplary implementations, isotope labeled fertilizer are employed. Performing an analysis of nitrogen isotopes (for example $^{15}N$) with an isotope ratio mass analyzer allows the user to determine what portion of the nitrogen measured in the chamber comes from the nitrogen fertilizer and also to help determine the processes driving the production of $N_2O$.

The measured mass extracted at each sampling time can be used to correct the gas concentrations within the chamber at later sampling intervals. As this correction might introduce a bias: by removing a sample of gas from the chamber the gas concentrations might be modified. If the sample volume is small—for example about 1% of the chamber volume, typically in the order of 20 L—such bias might be negligible. The bias due to sampling larger volumes can be reduced by waiting a longer time in order to allow the gas concentrations to equilibrate back to its initial concentration before sampling after each sampling event and redeploying to sample at a different time. Current practices to measure $N_2O$ fluxes typically include obtaining 3 samples, at 0, 15, and 30 minutes of chamber deployment each.

Certain alternative embodiments of the system 10 allow for the estimation of fossil fuel $CO_2$ soil mass flux. In these embodiments, samples are taken at different intervals as in the nitrogen fertilizer embodiments (above), except that a $CO_2$ sorbent such as soda lime, which is a strong base consisting of a mixture of calcium and sodium hydroxides and oxides, is utilized to sorb the $CO_2$ gas for further analysis. The samples obtained in these embodiments can be used to measure the total amount of carbonate—for example by using ASTM Method 4373-02 rapid determination for carbonates in soils—and for carbon isotopic analysis—such as by ASTM Method D-6866. In various implementations, standard test methods for determining the biobased content of solid, liquid, and gaseous samples such as radiocarbon analysis can be used to determine the fraction of carbon sorbed attributable to various sources, including fossil fuel LNAPL origin. In various implementations, field measurements for total $CO_2$ flux can also be taken with a gas analyzer in real time, while the fossil fuel $CO_2$ flux measurement can be used to determine the fossil fuel fraction of the flux based on field measurements that is fossil fuel. It is understood that in alternate implementations, several techniques can be used to deter In various implementations, the initial mass in the sorbent can be used to blank-correct the high volume samples taken from within the chamber 14. Multiple samples could be taken at different times, or at select times, such as initially and at the end of the chamber deployment. In these implementations, the mass of the sorbent is adjusted to the sample taken, so as the sorbed mass is large enough to be measurable and not so large that saturates the sorbent capacity.

According to certain alternative embodiments, the disclosed system and methods are used to estimate the in situ reaction rates for a reactive species. The approach consists of injecting a fixed volume of gas including known concentrations of both a non-reactive gas species—also known as a "tracer," such as sulfide hexafluoride, SF6—and a reactive species such as benzene. In these implementations, after injection, a volume of gas is retrieved from the chamber 14. The concentration profile of the tracer gas with time is used to estimate the in situ diffusion coefficients by solving for a transient effective diffusion equation as follows:

$$\frac{d}{dt}\left\{\left(\theta_v + \frac{\theta_w}{H_{tr}} + \frac{K_{s,tr}\rho_b}{H_{tr}}\right)C_{v,tr}\right\} = \nabla\left(D_{v,eff,tr} + \frac{D_{w,eff,tr}}{H_{tr}}\right)\nabla C_{v,tr} \quad \text{(Eq. 9)}$$

where H is the Henry's law constant,
Cv is the concentration in the vapor phase,
$\theta_v$ is the air-filled porosity of the soil,
$\theta_w$ is the water-filled porosity of the soil,
Ks is the sorption coefficient,
$\rho_b$ is the soil bulk density,
t is time,
$Dv_{,eff}$ is the vapor effective diffusion coefficient, and
$Dw_{,eff}$ is the water effective diffusion coefficients. Here, the subscript tr indicates that the parameters are specific for the tracer.

In certain implementations, measurement of the reactive species concentration over time is used to calculate the in situ reaction rate. In these implementations, the in situ reaction rate can be solved with the transient effective diffusion and reaction equation for the reactive species:

$$\frac{d}{dt}\left\{\left(\theta_v + \frac{\theta_w}{H_{rx}} + \frac{K_{s,rx}\rho_b}{H_{rx}}\right)C_{v,rx}\right\} = \nabla\left(D_{v,eff,rx} + \frac{D_{w,eff,rx}}{H_{rx}}\right)\nabla C_{v,rx} - k_{rx} \quad \text{(Eq. 10)}$$

where rx indicates that these parameters are specific to the reactive species.

In these circumstances, sorption coefficients for both the tracer and reactive species in soils would need independent estimation of sorption coefficienst $K_{s,rx}$ and $K_{s,tr}$, from laboratory experiments or empirical correlations (often based on the soil organic matter content.

The effective diffusion coefficient for the reactive species is independently calculated based on that of the tracer based on diffusion coefficients for both species in air:

$$D_{v,eff,rx} = D_{v,eff,tr}\left(\frac{D_{air,rx}}{D_{air,tr}}\right) \quad \text{(Eq. 11)}$$

Thus, by solving Eq. 9 first for the tracer species, the only unknown in Eq. 10 is the in situ reaction rate for the reactive species. This unknown would be obtained by fitting the solution to Eq. 10 to a data set obtained using the systems and methods disclosed herein.

Implementations of the system 10 using isotope-labeled compounds have advantages when the reactive species is already present at the soil location. By using isotope-labeled compounds, for example deuterated benzene if normal benzene is already present in the soil. the procedure allows for the estimation of the reaction rate of the isotope-labeled compound.

Figure 8:
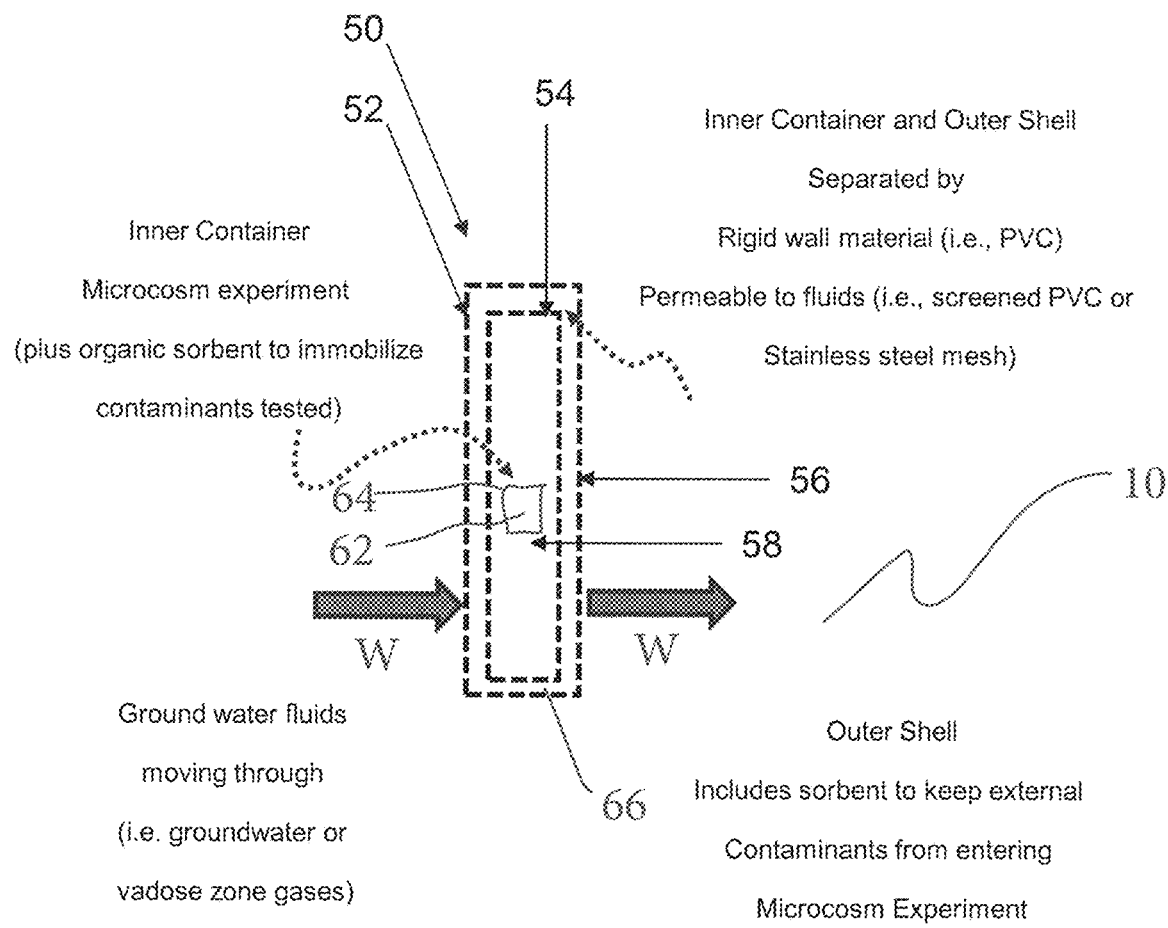
FIG. 8 is a schematic side view of an implementation of a multi-chambered device, according to an exemplary implementation of the system.
Figure 9:
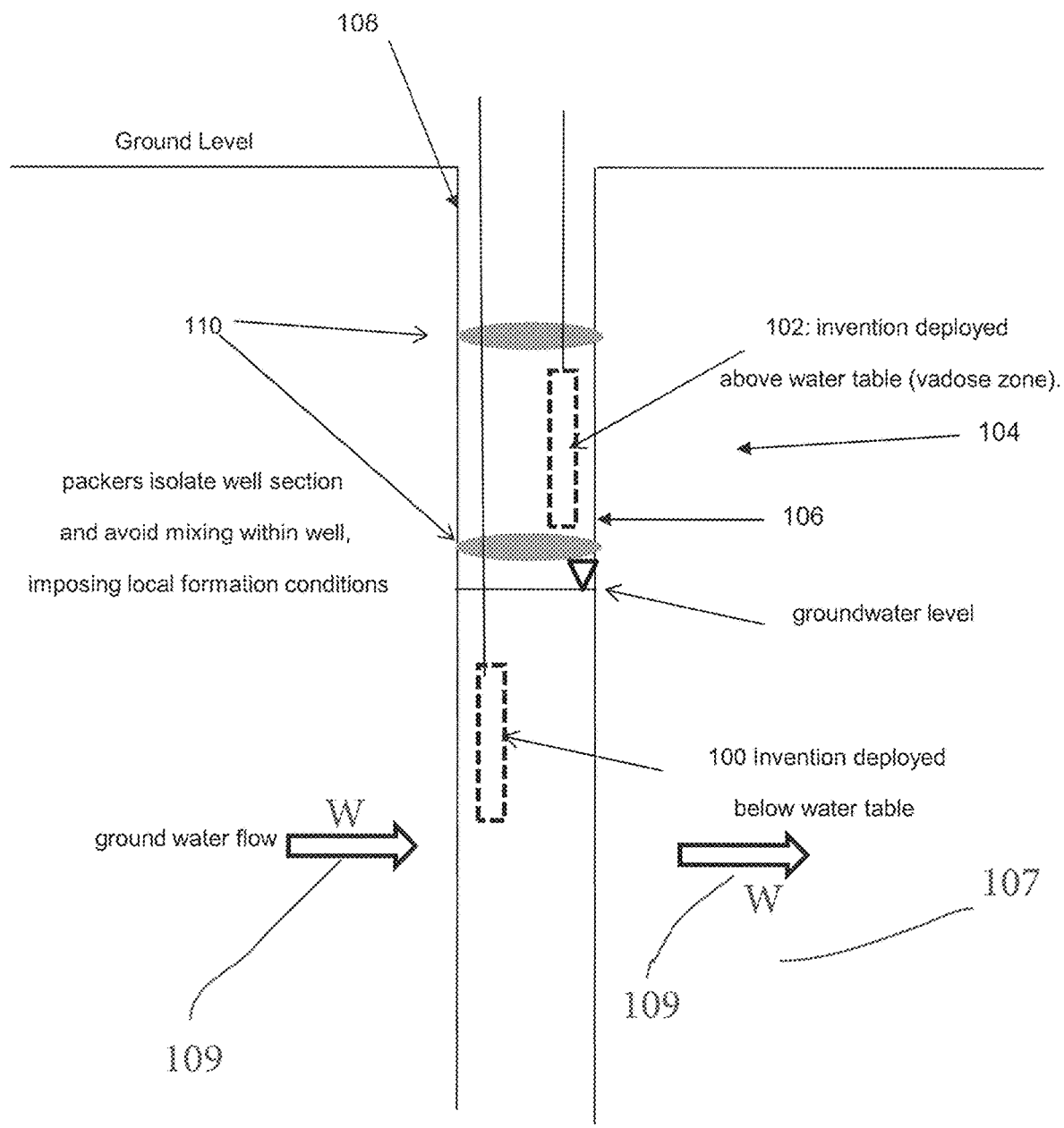
FIG. 9 is a schematic side view of an implementation of selectively-permeable chamber devices deployed in and below the vadose zone according to an exemplary implementation of the system.

Certain alternative exemplary embodiments of the system relate to apparatus, systems and methods for conducting microcosm studies in situ that enable direct estimates of the degradation rate of specific soil contaminants by using selectively permeable chambers 14. As is shown in FIGS. 8-9, in these "compound specific" embodiments, an in situ device 50, 100 is generally deployed in the soil adjacent to contamination, either in preexisting wells or in wells specifically emplaced for deployment of the device 50, 100. In exemplary implementations of the system employing the in situ device 50, 100, the device 50, 100 does not require gaseous communication, but instead is able to assess the flux of certain species of interest using chemical and physical approaches described herein.

FIG. 8 depicts a schematic overview of one implementation of a passive in situ measurement system 10 comprising an in situ device 50 that is a double-wall container. In the double wall container device 50 has an inner container 52 and an outer shell 54. In certain embodiments, both the inner container 52 and outer shell 54 are fluidically and/or gaseously permeable, so as to allow flow of either groundwater (shown at reference arrows W), gases, or both according to the location where it is deployed. In exemplary embodiments, the inner container 52 and outer shell 54 are separated by a rigid wall material and are permeable to fluids, such as screened PVC, stainless steel mesh, and/or a semipermeable membrane. Accordingly, exemplary embodiments of the approach are "closed," and thereby divide and isolate the soil as is described herein.

In the implementation of FIG. 8, both the inner container 52 and the outer shell 54 allow the flow through of fluids (shown by reference arrow W). Further, in this implementation, the inner container 52 includes a second opening 58 which contains native soil that is seeded (or "spiked")—spiked soil 62—with a known amount of the contaminant or contaminants of interest. In certain embodiments, the spiked soil 62 can contain contaminants before the spike, without compromising the feasibility of the quantization of the degradation rate, as long as the initial mass is known. In exemplary embodiments of the approach, the contaminants are immobilized within the inner wall 52 by way of a solid sorbent 64, such that the contaminants remain in the inner container 52 and do not substantially partition into the fluids that are free to move through the device. It is understood that organic sorbents may be used. Exemplary sorbents include polymers typically used in chemical analysis to concentrate large volume samples or their pyrolysis products, such as XAD, carbotrap, carbosieve, carboxen—as well as carbonaceous materials such as carbon black, or activated carbon.

In exemplary embodiments, at least one opening 56 is present between the outer shell 54 and inner container 52. It is understood that in certain implementations the opening 56 can refer to generally to the openings in permeable materials, such as stainless steel mesh. In these embodiments, a second sorbent 66 such as activated carbon is disposed within the opening 56, thereby keeping native soil contaminants from coming into contact with the sorbent of the inner container. In this way, the approach works as a closed system for contaminants, such that there is minimal passage of contaminants between the various regions, but open to the native soil fluid components, such as moisture levels, geochemistry, electron acceptors, microbial nutrients, and otherwise at native soil conditions such as temperature and pressure. The contaminant degradation rates are expressed as half-lives, and can thus be determined as a function of the changes in concentration over time within the inner container at conditions typical of soil at the location of deployment of the device. In certain alternate implementations, the fluid permeable inner container 52 and outer shell 54 can be with a membrane that is selectively, or semi-permeable to ions and small molecules but impermeable to organics, such as Nafion or Celgard. In certain of these alternate implementations, a sorbent may not be required.

Microbial biomass typically consists of the native microbes existing in the soil before the sample is obtained. In various implementations, abiotic or non-reactive controls are needed so as to demonstrate that such measured contaminant degradation/losses are not due to losses resulting from other causes, such as flow-through fluids. For example, one such control can be achieved by adding a microbial inhibitor—such as formaldehyde—to the inner container 52. This substance would be sorbed in the same manner as the contaminants of interest, so it is not lost to partitioning into the fluids moving through the device.

FIG. 9 is a side view schematic depicting the deployment of in situ microcosm devices 100, 102 with double wall design within a screened well, according to one embodiment. As is depicted in this embodiment, a first device 100 is emplaced below the water table 107, while a second device 102 is placed in the vadose zone 104. The second device 102 is emplaced in the vadose zone 1 an isolated section 106 of the well 108 with packers 110 to achieve local conditions in formation, rather than those from mixing within well space. As discussed above, additional abiotic controls can be deployed by adding microbial inhibitor, such as formaldehyde.

Microcosm studies conducted in the laboratory have been established to determine contaminant degradation rates, but these methods present limitations as they are not typically representative of field conditions. In situ microcosm studies have been developed more recently by placing a soil container with selectively- or semi-permeable walls within wells in the soil (as for example, commercialized by Microbial Insights). In these methods, the samples are retrieved and analyzed microbially, such as for genetic material indicative of the type of bacteria colonizing the container. These microcosm studies can provide useful qualitative information about the type of processes relevant to contaminant degradation occurring in soils. These techniques have gone as far as "spiking" the container with a known amount of isotope-labeled contaminants, such as carbon isotopes. The limitation is that these approaches do not account for the biodegradation byproducts which are not incorporated into the microbial biomass—such as carbon dioxide or methane—which typically leave with the fluids flowing through the device.

By measuring the carbon uptake by the microbial biomass, it is possible to estimate the rate of microbial degradation of, for example, soil contaminants. For reference, an example equation for the aerobic biodegradation of benzene is given by:

$$C_6H_6 + H_2O \rightarrow CO_2 + \text{Biomass} \tag{Eq. 12}$$

A second example consists of the abiotic in situ degradation of chlorinated organics such as dichloroethene, $C_2H_2Cl_2$. This abiotic in situ degradation is due to iron oxides and hydroxides (such as green rust, also known as Fougerite), and results in the production of dechlorinated by-products such as acetylene, ethylene, or ethane. Such a reaction can be described by the following:

$$C_2H_2Cl_2 + Fe_2(OH)_{12}CO_3 \rightarrow \text{dechlorinated by-products} + 2Cl^- \tag{Eq. 13}$$

In prior art methods, generation of by-products is the major mechanism for assessment. This is because microbial biomass in soils achieves a steady state—meaning it does not change significantly after at reaches a certain level. Thus, existing approaches for mass balance on the contaminant biodegraded material are incomplete. An additional limitation in certain prior art approaches is the high cost of the isotope-labeled contaminants.

The various embodiments of the system 10 having an in situ device 50, 100 described herein allow for a mass balance calculation on the added, or "spiked" contaminant, so as to measure the difference between the initial and final concentrations and better reflect the activity directly, rather than on the basis of by-products. In these implementations, it is understood that by "spiked," the contaminants in these implementations can be either non-labeled or isotope-labeled. In certain of these implementations, the initial concentrations of the materials are representative of those in the native soil based on previous soil or water analysis at the site, and can be used as "worse-case scenarios" for risk assessment. It is further understood that the disclosed embodiments provide a direct measure of degradation rates regardless of whether such losses are due to either of the different mechanisms of incorporating contaminant mass into biomass or generation of biodegradation products.

Although the disclosure has been described with reference to preferred embodiments, persons skilled in the art will recognize that changes may be made in form and detail without departing from the spirit and scope of the disclosed apparatus, systems and methods.

What is claimed is:

1. A system for in situ measurement of gas flux through porous media comprising:
   a. a chamber emplaced within a permeable region of a well within a porous media, wherein the chamber is flushed with at least one inert gas;
   b. a gas concentration device configured to measure responses of the device equilibrated with the porous material;
   c. a pressure sensor disposed within the chamber; and
   d. a double-walled container configured to be disposed within the chamber, the double-walled container comprising:
      i. an outer shell and
      ii. an inner container,
   wherein perturbations in pressure and/or concentrations measure the porous material gas flux, and wherein the doubled-walled container is semi-permeable.

2. The system of claim 1, wherein the gas concentration device is further configured to establish initial concentration and pressure and configured to estimate advective fluxes.

3. The system of claim 1, wherein the system is configured to flush the chamber with inert gas and then measure change in concentration of a gas species over time.

4. The system of claim 1, wherein a sorbent is disposed in the inner container.

5. The system of claim 1, further comprising a seeded soil disposed within the inner container, the seeded soil comprising a known amount of a contaminant.

6. The system of claim 5, further comprising a solid sorbent disposed within the inner container.

7. A method for in situ measurement of porous media mass fluxes, comprising:
   a. emplacing a chamber in a medium of interest, wherein the chamber is in operable communication with a pressure sensor, and wherein the chamber comprises a selectively-permeable outer shell disposed around a selectively-permeable inner container,
   b. flushing the chamber with at least one inert gas to decrease the concentration of a species of interest,
   c. establishing a flux of at least one gas of interest by way of the change in concentration of a species over time in the chamber,
   d. equilibrating the chamber with the porous media prior to perturbation, and
   e. calculating the flux without the knowledge of porous media properties.

8. The method of claim 7, wherein the chamber is in operable communication with a gas concentration meter.

9. The method of claim 7, wherein the chamber is in operable communication with a plurality of conduits leading out of the chamber.

10. The method of claim 7, further comprising:
    a. establishing a pressure inside the chamber and a concentration of at least one gas of interest; and
    b. flushing the chamber with inert gas by way of at least one conduit.

11. The method of claim 7, further comprising sorbing a species of interest by a sorbent, the sorbent disposed within the selectively-permeable inner container.

12. The method of claim 11, wherein the sorbent is at least one of XAD, carbotrap, carbosieve, carboxen, carbon black, and activated carbon.

13. A device for in situ microcosm studies, to include microbial reactions, in porous media, comprising:
    a. a double walled container further comprising an inner container and an outer shell configured to be disposed in the media;
    b. the inner container defining an inner opening;
    c. a void defined between the inner container and the outer shell; and
    d. a first sorbent disposed within the inner opening,
    e. the void is filled with a second sorbent,
    wherein the inner container and outer shell are selectively permeable, so as to allow flow of at least one of groundwater and gases through the container, and wherein the first sorbent is capable of stabilizing a gas sample.

14. The method of claim 13, wherein the first sorbent comprises at least one of zeolites, minerals, soda lime, sodium hydroxides, sodium oxides, calcium hydroxides, and calcium oxides.

15. The device of claim 13, further comprising a contaminant of interest, further comprising a native media seeded with the contaminant of interest disposed within the inner opening.

16. The device of claim 15, wherein the contaminant is immobilized within the inner opening by way of the first sorbent such that the contaminants remain in the inner container.

17. The device of claim 13, wherein the first sorbent is spiked.

18. The device of claim 17, wherein the inner container contains a known quantity of substrate for microbial population.

19. The device of claim 17, further comprising a processor configured to calculates mass balance and biodegradation rates.

* * * * *